(12) United States Patent
Chung et al.

(10) Patent No.: US 8,753,606 B2
(45) Date of Patent: Jun. 17, 2014

(54) MULTIMODAL IMAGING METHOD USING NANO-EMULSION COMPRISING OPTICAL NANO-PARTICLES AND PERFLUOROCARBONS

(75) Inventors: Bong Hyun Chung, Daejeon (KR); Yong Taik Lim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 459 days.

(21) Appl. No.: 13/000,197

(22) PCT Filed: Jun. 19, 2009

(86) PCT No.: PCT/KR2009/003308
§ 371 (c)(1),
(2), (4) Date: Dec. 20, 2010

(87) PCT Pub. No.: WO2009/154425
PCT Pub. Date: Dec. 23, 2009

(65) Prior Publication Data
US 2011/0110867 A1    May 12, 2011

(30) Foreign Application Priority Data
Jun. 21, 2008    (KR) .................. 10-2008-0058687

(51) Int. Cl.
*A61K 49/00*    (2006.01)
(52) U.S. Cl.
USPC ........................................................ 424/9.1
(58) Field of Classification Search
USPC ........................................................ 424/9.1
See application file for complete search history.

(56) References Cited

U.S. PATENT DOCUMENTS

| | | |
|---|---|---|
| 5,080,885 A | 1/1992 | Long et al. |
| 6,548,046 B1 | 4/2003 | Lanza et al. |
| 6,676,963 B1 | 1/2004 | Lanza et al. |
| 8,568,690 B2 * | 10/2013 | Lu et al. .................. 424/9.1 |
| 2003/0086867 A1 | 5/2003 | Park et al. |
| 2003/0215392 A1 | 11/2003 | Lanza et al. |
| 2004/0115192 A1 | 6/2004 | Lanza et al. |
| 2004/0248856 A1 | 12/2004 | Lanza et al. |
| 2007/0092447 A1 | 4/2007 | Padilla De Jesus et al. |
| 2007/0253910 A1 * | 11/2007 | Ahrens et al. ............ 424/9.34 |

OTHER PUBLICATIONS

Caravan, P., "Strategies for increasing the sensitivity of gadolinium based MRI contrast agents", Chemical Society Reviews 35:512-523, 2006.
Bulte, et al., "Iron oxide MR contrast agents for molecular and cellular imaging", NMR in Biomedicine 17:484-499, 2004.
Yang, et al., "GdIII-functionalized fluorescent quantum dots as multimodal imaging probes", Advanced materials 18:2890-2894, 2006.
Yu, et al., "19F: A versatile reporter for non-invasive physiology and pharmacology using magnetic resonance", Curr. Med. Chem. 12:819-848, 2005.
Flacke, et al., "Novel MRI contrast agent for molecular imaging of fibrin implications for detecting vulnerable plaques", Circulation, 104:1280, 2001.
Winter, et al., "Improved molecular imaging contrast agent for detection of human thrombus", Magnetic Resonance in Medicine. 50:411-416, 2003.

* cited by examiner

*Primary Examiner* — Michael G Hartley
*Assistant Examiner* — Melissa Perreira
(74) *Attorney, Agent, or Firm* — Lucas & Mercanti, LLP

(57) ABSTRACT

The present invention relates to a multimodal imaging method using a nano-emulsion comprising optical nano-particles and perfluorocarbons, and more particularly, to a method of obtaining multimodal images using a nano-emulsion consisted of perfluorocarbons for multispectral magnetic resonance imaging (MRI) and nano-particles for multicolor fluorescent detection. In the multimodal imaging method, various multispectral MRI images and multicolor fluorescent rays can be obtained by varying the kind and combination of perfluorocarbons and the kind and combination of optical nano-particles, so that multiplexed analysis is possible. Accordingly, the multimodal imaging method can be applied to various fields, including biological and medical fields in which studies on cell molecular imaging has been conducted.

11 Claims, 3 Drawing Sheets

MULTIMODAL IMAGING METHOD USING NANO-EMULSION COMPRISING OPTICAL NANO-PARTICLES AND PERFLUOROCARBONS

CROSS-REFERENCE TO RELATED APPLICATIONS

This application is a 371 of PCT/KR2009/003308 filed on Jun. 19, 2009, which claims the benefit of Korean Application No. 10-2008-0058687 filed on Jun. 21, 2008, the contents of each of which are incorporated herein by reference.

TECHNICAL FIELD

The present invention relates to a multimodal imaging method using a nano-emulsion comprising optical nano-particles and perfluorocarbons, and more particularly, to a method of obtaining multimodal images using a nano-emulsion comprising perfluorocarbons for multispectral magnetic resonance imaging and optical nano-particles for multicolor fluorescent detection.

BACKGROUND ART

Magnetic resonance imaging (MRI) techniques have been widely applied in actual clinical fields because high-resolution images can be rapidly obtained. Currently, two kinds of contrast agents is used in the MRI field so as to amplify hydrogen ($^1$H)-based MRI signals. The first contrast agent, as a T1-based contrast agent, is used a para-magnetic gadolinium (Gd) or manganese (Mn)-based material, and the second contrast agent, as a T2-based contrast agent, is used a superparamagnetic iron oxide-based material. However, the T1-based contrast agent is harmful to human bodies because its concentration is high to obtain desired image signals in actual clinical fields (Caravan, P. Strategies for increasing the sensitivity of gadolinium based MRI contrast agents. Chemical Society reviews 35, 512-523 (2006)), the T2-based contrast agent has difficulty in obtaining image signals because frequency shifts may be caused by the T2-based contrast agent (Bulte, J. W. & Kraitchman, D. L. Iron oxide MR contrast agents for molecular and cellular imaging. NMR in biomedicine 17, 484-499 (2004)). Further, the techniques using such the $^1$H-based MRI cannot obtain multiplexed analysis images as compared with the techniques using optical imaging contrast agents which can emit various wavelengths.

Furthermore, the MRI techniques have a lower sensitivity than an imaging technique such as poistron emission tomography (PET) or single-photon emission computerized tomography (SPECT).

To solve theses problems, bimodal imaging contrast agents have been actively studied, which can measure both optical and magnetic properties by coupling fluorescent materials, such as organic fluorescent dyes or quantum dot nano-particles, with an MRI contrast agent (Mulder, W. J. et al. Magnetic and fluorescent nanoparticles for multimodality imaging. Nanomedicine 2, 307-324 (2007), Uzgiris, E. E. et al. A multimodal contrast agent for preoperative MR Imaging and intraoperative tumor margin delineation. Technology in cancer research & treatment 5, 301-309 (2006), Yang, H., Santra, S., Walter, G. A. & Holloway, P. H. GdIII-functionalized fluorescent quantum dots as multimodal imaging probes. Advanced materials 18, 2890-2894 (2006)).

Meanwhile, perfluorocarbon (PFC) is an excellent material for MRI contrasting, the PFC and derivatives thereof have been actively studied in $^{19}$F MRI fields. As compared with conventional $^1$H MRI contrast agents, $^{19}$F has an almost identical gyromagnetic ratio to protons, a spin ½ nucleus and 100% of natural abundance. Further, $^{19}$F is harmless to human bodies with a background concentration (Yu, J. X., V. D., Cui, W. & Mason, R. P. 19F: A versatile reporter for non-invasive physiology and pharmacology using magnetic resonance. Curr. Med. Chem. 12, 819-848 (2005)).

PFC emulsion nano-particles may be functionalized as a MR molecular imaging by bonding paramagnetic chelates and homing ligands onto an external phospholipid monolayer in MRI field, and many studies of the PFC emulsion nano-particles have been conducted as drug delivery vectors including bioactive agents (US 2004/0115192 A1; U.S. Pat. No. 6,676,963B1; US 2003/0086867; US 2003/0215392 A1; US 2004/0248856 A1). In the MRI, the nuclei are dephased and then rearranged in the direction of a magnetic field. At this time, the process of supplying energy to the lattice of the nuclei to reach a thermal equilibrium is referred to as T1. The PFC emulsion nano-particles are used as T1-weighted ultra-paramagnetic contrast agents reflected in particulate or molecular relaxivity.

In this case, the contrast ratio should be maximum so that the contrast agents are seen more distinctly than neighboring normal portions. To this end, the contrast agents are required to have maximum relaxivity. For the contrast agents to have maximum relaxivity, all the paramagnetic materials used as the contrast agents are necessarily in an external aqueous phase. In 1.5 T, the molecular relaxivity of the PFC nano-particles depends on lipophilic chelates and has a value of 1,000,000 to 2,000,000 mMs$^{-1}$ (Flacke et al, Circulation, 104:1280, 2001; Winter et al, Magn. Reson. med., 50:411, 2003).

The fluorescent MRI contrast agent known until now is a perfluorocarbon nano-emulsion containing fluorescent nano-particles. There are known a method using the magnetic resonance property of $^{19}$F in the nano-emulsion itself and a method of injecting a contrast agent for $^1$H MR into PFC emulsion nano-particles by adding a chelating agent of gadolinimum (Gd) for $^1$H magnetic resonance to a lipid layer that surrounds the PFC emulsion nano-particles.

However, the conventional fluorescent contrast agents for MRI emit only a single color or a single resonance frequency, and therefore, only a single disease can be detected.

Accordingly, the present inventors have prepared a nano-emulsion obtained by combining each perfluorocarbon having a unique resonance frequency and derivatives thereof with each quantum dot nano-particle emitting multifluorescent rays, and have verified that multispectral MRI and multi-color fluorescent rays are obtained depending on the combination of the perfluorocarbon and its derivatives and the quantum dot nano-particles, therefore multiplexed analysis being possible.

DISCLOSURE OF INVENTION

Technical Problem

An object of the present invention is to provide a multimodal imaging method using a nano-emulsion comprising optical nano-particles and perfluorocarbons.

Technical Solution

To achieve this object of the present invention, there is provided a multimodal imaging method of simultaneously obtaining multispectral magnetic resonance imaging and multi-color fluorescent rays by varying the kind or combination of optical nano-particles and perfulorocarbons using a nano-emulsion consisted of the optical nano-particles and the perfluorocarbons.

Advantageous Effects

According to the present invention, since a nano-emulsion comprising optical nano-particles and perfluorocarbons simultaneously has optical and $^{19}F$ magnetic resonance characteristics, multispectral MRI images and multicolor fluorescent rays are obtained by varying the kind and combination of the perfluorocarbons, so that multiplexed analysis can be possible based on the obtained results. Therefore, in the multimodal imaging method of the present invention, optical nano-particles and perfluorocarbons are respectively capped with different materials, thereby detecting various target materials corresponding to the number of combinations of the capped materials. Accordingly, the multimodal imaging method of the present invention can be applied to various fields, including biological and medical fields in which studies on cell molecular imaging has been conducted.

BEST MODE FOR CARRYING OUT THE INVENTION

Hereinafter, the present invention will be described in detail.

The present invention provides a multimodal imaging method in vivo using a nano-emulsion comprising optical nano-particles and perfluorocarbons, which comprises injecting the nano-emulsion in vivo to simultaneously perform multicolor ray emission of the optical nano-particles and control of resonance frequencies in accordance with the kinds of perfluorocarbons (a first step); and measuring the combined wavelength of the emitted rays and the controlled resonance frequency of the perfluorocarbons (a second step).

The first step is a step of inducing different multimodal images by simultaneously performing emission of multicolor rays through combination of optical nano-particles capped with a material and a target material in vivo and control of resonance frequencies through combination of perfluorocarbons capped with another material and the corresponding target material to allow the emitted wavelengths to overlap with the controlled resonance frequencies.

In the multimodal imaging method, m×n multimodal images can be simultaneously obtained using combinations of multispectral MRI images and multicolor fluorescent rays, which obtained by combinations of the number (m) of kinds of the perfluorocarbons and the number (n) of the multicolor fluorescent rays generated from optical nano-particles.

Figure 1:
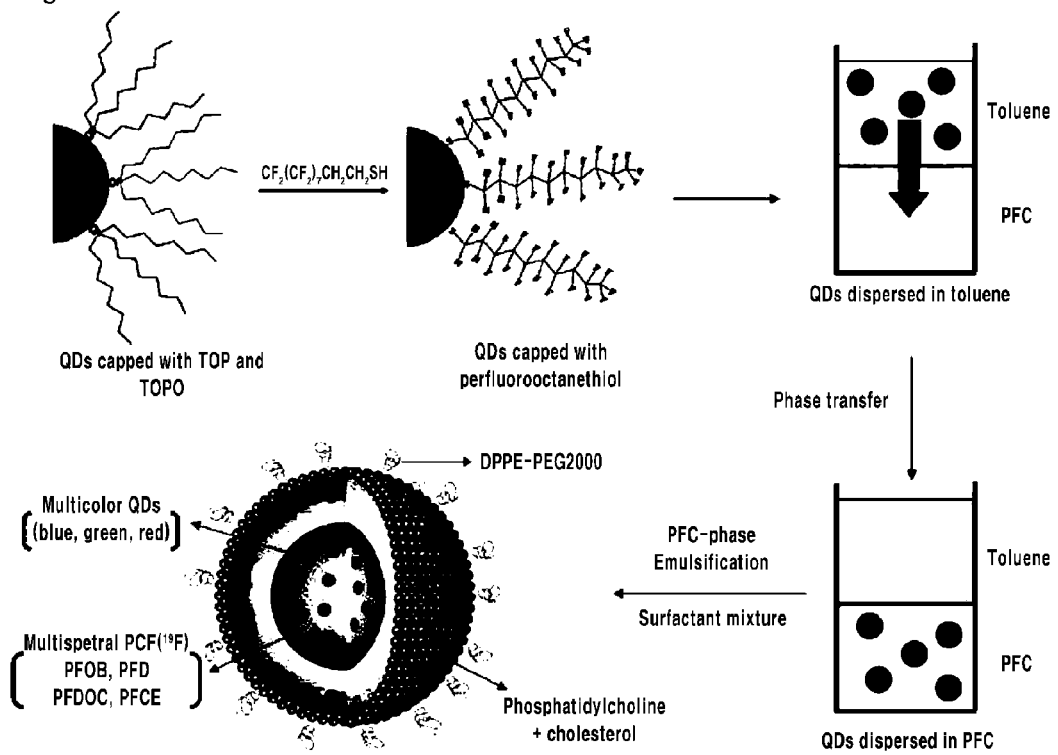
FIG. 1 is a schematic view illustrating a nano-material capable of simultaneously detecting multispectral magnetic resonance imaging (MRI) and multicolor fluorescent rays and a preparation method thereof.

The nano-emulsion may be prepared by the following method comprising:

1) performing surface reforming by allowing optical nano-particles coated with hydrocarbon to be coated with perfluorocarbons;

2) allowing the optical nano-particles surface-reformed at the step 1) to be dispersed into a perfluorocarbon liquid; and 3) emulsifying the liquid at the step 2). However the present invention is not limited thereto (see FIG. 1).

In the method, the optical nano-particles at the step 1) may be quantum dot nano-particles, organic fluorescent dyes or metal nano-particles. However, the present invention is not limited thereto.

The quantum dot nano-particles may be consisted of II-VI or III-V compounds in the periodic table. Preferably, the quantum dot nano-particle may be selected from the group consisting of a single core and a core/shell. More preferably, the quantum dot nano-particle may be selected from the group consisting of CdSe, CdSe/ZnS, CdTe/CdS, CdTe/CdTe, ZnSe/ZnS, ZnTe/ZnSe, PbSe, PbS, InAs, InP, InGaP, InGaP/ZnS and HgTe. However, the present invention is not limited thereto.

Further, the optical nano-particles at the step 1) may include metal nano-particles having light absorption and scattering properties, such as multicolor gold or silver.

Preferably, the surface of the quantum dot nano-particle in the nano-emulsion is reformed with a perfluorocarbon for surface reforming, and the perfluorocarbon containing the reformed quantum dot nano-particle is encapsulated in a lipid liposome.

Preferably, the perfluorocarbon for surface reforming includes perfluorochemical having one end group selected from the group consisting of thiol, phosphine and phosphine oxide, or amphiphilic fluorinated hydrocarbon. More preferably, the perfluorocarbon for surface reforming includes one selected from the group consisting of perfluorinated alcohol phosphate ester and its salt, perfluorinated sulfonamide alcohol phosphate ester and its salt, perfluorinated alkyl sulfonamide alkylene quaternary ammonium salt, N,N-(carboxyl-substituted lower alkyl) perfluorinated alkyl sulfonamide, and a compound thereof. However, the present invention is not limited thereto.

The perfluorinated alcohol phosphate ester may include a free acid of mono or bis(1H,1H,2H,2H-perfluoroalkyl)phosphate derived diethanolamine salt. However, the present invention is not limited thereto.

The perfluorinated sulfonamide alcohol phosphate ester may be one selected from the group consisting of perfluoro-n-octyl-N-ethysulfonamidoethyl phosphate, bis(perfluoro-n-octyl-N-ethylsulfonamidoethyl)phosphate, ammonium salt of bis(perfluoro-n-octyl-N-ethylsulfonamidoethyl)phosphate, bis(perfluorodecyl-N-ethylsulfonamidoethyl phosphate and bis(perfluorohexy-N-ethylsulfonamidoethyl)phosphate. However, the present invention is not limited thereto.

The nano-emulsion has multispectral magnetic resonance images obtained by varying the kind of perfluorocarbon derivatives containing $^{19}F$ or their combination.

Preferably, the perfluorocarbon containing $^{19}F$ at the step 2) includes at least one functional group connected to a main chain consisting of carbon atoms. More preferably, the perfluorocarbon containing $^{19}F$ is one selected from the group consisting of perfluorotributylamine (FC47), perfluorodecalin (PP5), perfluoromethyldecalin (PP9), perfluorooctylbromide, perfluorotetrahydrofuran (FC80), perfluoroether (PID) [(CF$_3$)$_2$CFOCF$_2$(CF$_2$)$_2$CF$_2$OCF(CF$_3$)$_2$], perfluoroether (PIID) [(CF$_3$)$_2$CFOCF$_2$(CF$_2$)$_6$CF$_2$OCF(CF$_3$)$_2$], perfluoroetherpolymer (Fomblin Y/01), perfluorododecane, perfluorobicyclo[4.3.0]nonane, perfluorotritrimethylbicyclohexane, perfluorotripropylamine, perfluoroisopropylcyclohexane, perfluoroendotetrahydrodicyclopentadiene, perfluoroadamantane, perfluoroexotetrahydrodicyclopentadiene, perfluorobicyclo[5.3.0]decane, perfluorotetramethylcyclohexane, perfluoro-1-methyl-4-isopropylcyclohexane, perfluoro-n-butylcyclohexane, perfluorodimethylbicyclo[3.3.1]nonane, perfluoro-1-methyl-4-t-butylcyclohexene, perfluorodecahydroacenapthene, perfluoro-nundecane, perfluorotetradecahydrophenanthrene, perfluoro-1,3,5,7-tetramethyladamantane, perfluorododecahydrofluorene, perfluoro-1-3-dimethyladamantane, perfluoro-n-octylcyclohexane, perfluoro-7-methyl bicyclo[4.3.0]nonane, perfluoro-p-diisopropylcyclohexane, perfluoro-m-diisopropylcyclohexane, perfluoro-4-methyloctahydroquinolidizine, perfluoro-N-methyldecahydroquinoline, F-methyl-1-oxadecalin, perfluorooctahydroquinolidizine, perfluoro 5,6-dihydro-5-decene, perfluoro-4,5-dihydro-4-octene, perfluorodichlorooctane, perfluorobischlorobutyl ether, perfluorooctane, perfluorodichlorooctane, perfluoro-n-octylbromide, perfluoroheptane, perfluorodecane, perfluorocyclohexane, perfluoromorpholine, perfluorotripropylamine, perfluorotributylamine, perfluorodimethylcyclohexane, perfluorotrimethylcyclohexane, perfluorodicyclohexylether, perfluoro-n-butyltetrahydrofuran, perfluoro-15-crown-5ether and compounds structurally similar thereto. However, the present invention is not limited thereto.

In the method, the emulsification at the step 3) may be performed using one or more selected from the group consisting of homogenizer, sonication and high shear force. However, the present invention is not limited thereto.

In the nano-emulsion of the present invention, a perfluorocarbon solution containing quantum dot nano-particles as optical nano-particles may be is encapsulated in a lipid liposome that forms an external layer using a lipid/surfactant. However, the present invention is not limited thereto.

The lipid having an external layer that coats the perfluorocarbon solution may be selected from the group consisting of natural or synthetic phospholipid, fatty acids, cholesterols, lysolipids, sphingomyelins, tocopherols, glucolipid, stearylamines, cardiolipins, plasmalogens, lipid with ether or ester linked fatty acids, and polymerized lipids.

The surfactant having an external layer that coats the perfluorocarbon solution may be selected from the group consisting of an anionic surfactant, a cationic surfactant, a nonionic surfactant and an amphoteric surfactant. However, the present invention is not limited thereto.

Preferably, the surfactant is one or more selected from the group consisting of an anionic surfactant, a cationic surfactant, a nonionic surfactant and an amphoteric surfactant, which are commercially used. More preferably, the surfactant is one or more selected from the group consisting of Pluronic F-68, Hamposyl™ L30, sodium dodecyl sulfate, Aerosol 413, Aerosol 200, Lipoproteol™ LCO, Standapol™ LCO, Standapol™ SH 135, Fizul™ 10-127, Cyclopol™ SBFA 30, Deriphat™ 170, Lonzaine™ JS, Niranol™ C2N-SF, Amphoterge™ W2, Amphoterge™ 2WAS, Pluronic™ F-68, Pluronic™ F-127, Brij™ 35, Triton™ X-100, Brij™ 52, Span™ 20, Generol™ 122 ES, Triton™ N-42, Triton™ N-101, Triton™ X-405, Tween™ 80, Tween™ 85 and Brij™ 56. However, the present invention is not limited thereto.

The perfluorocarbon nano-emulsion containing optical nano-particles may be used by allowing aptamers or nucleic acids to attach the surface of the nano-particle or to conjugate the nano-particle using cationic lipids.

The cationic lipid may be one selected from the group consisting of N-[1-(2,3-dioleoyloxy)propyl]-N,N,N-trimethylammonium chloride (DOTMA), 1,2-dioleoyloxy-3-(trimethylammonio)propane (DOTAP), 1,2-dioleoyl-3-(4'-trimethyl-ammonio)butanoyl-sn-glycerol (DOTB), 1,2-diacyl-3-dimethylammonium-propane (DAP), 1,2-diacyl-3-trimethylammonium-propane (TAP), 1,2-diacyl-sn-glycerol-3-ethylphosphocholine, 3β-(N',N'-dimethylaminoethane)-carbamolcholestrol-HCl, DC-Cholesterol, and dimethyldioctadecylammonium bromide (DDAB). However, the present invention is not limited thereto.

The present inventors have found magnetic resonance imaging and multicolor fluorescent characteristics for a nano-emulsion comprising optical nano-particles and perfluorocarbons.

Figure 2:
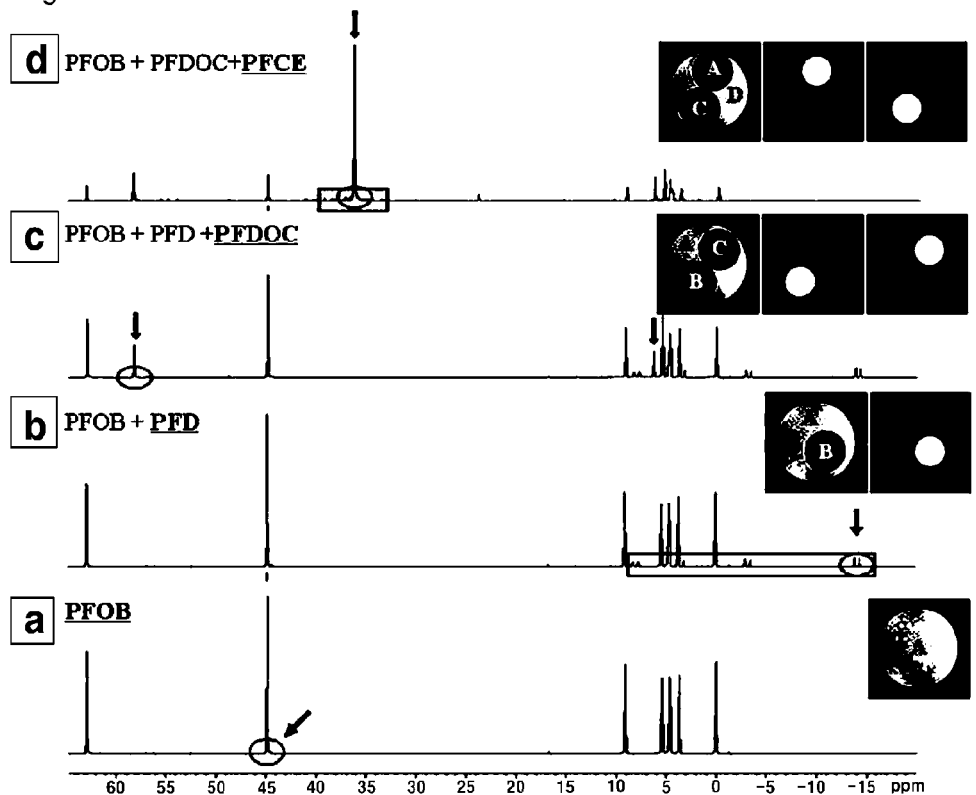
FIG. 2 illustrates magnetic resonance spectra and images of four kinds of perfluoro materials used as multispectral MRI contrast agents [(a) PFOB, (b) PFOB+PFD mixture, (c) PFOB+PFD+PFDOC mixture, and (d) PFOB+PFDOC+PFCE mixtuure].

As a result obtained by analyzing MRI characteristics for four kinds of perfluorocarbons, it can be seen that magnetic resonance spectral characteristics and images for the four kinds of perfluorocarbons are different from one another (see FIG. 2). Also, the nano-emulsion of the present invention shows selective MRI images in accordance with perfluorocarbons used. Accordingly, the present inventors have verified the multispectral MRI characteristics (see FIG. 4).

Further, as a result obtained by analyzing optical characteristics for the nano-emulsion, the nano-emulsion shows fluorescent characteristics with respect to red, green and blue filters. Accordingly, the present inventors have verified the multicolor fluorescent characteristics (see FIG. 4).

That is, multimodal imaging is obtained by combinations of multispectral MRI and multicolor fluorescent rays. Here, the multispectral MRI is obtained by varying the kind of perfluorcarbon derivatives containing $^{19}$F and their combination, and the multicolor fluorescent rays obtained by varying the kind of optical nano-particles and their combination.

MODE FOR THE INVENTION

Hereinafter, the present invention will be described in more detail with reference to the following examples.

These examples are provided for illustrative purposes only. It will be appreciated that various modifications can be made to these examples without departing from the scope of the present invention.

Example 1

Figure 3:
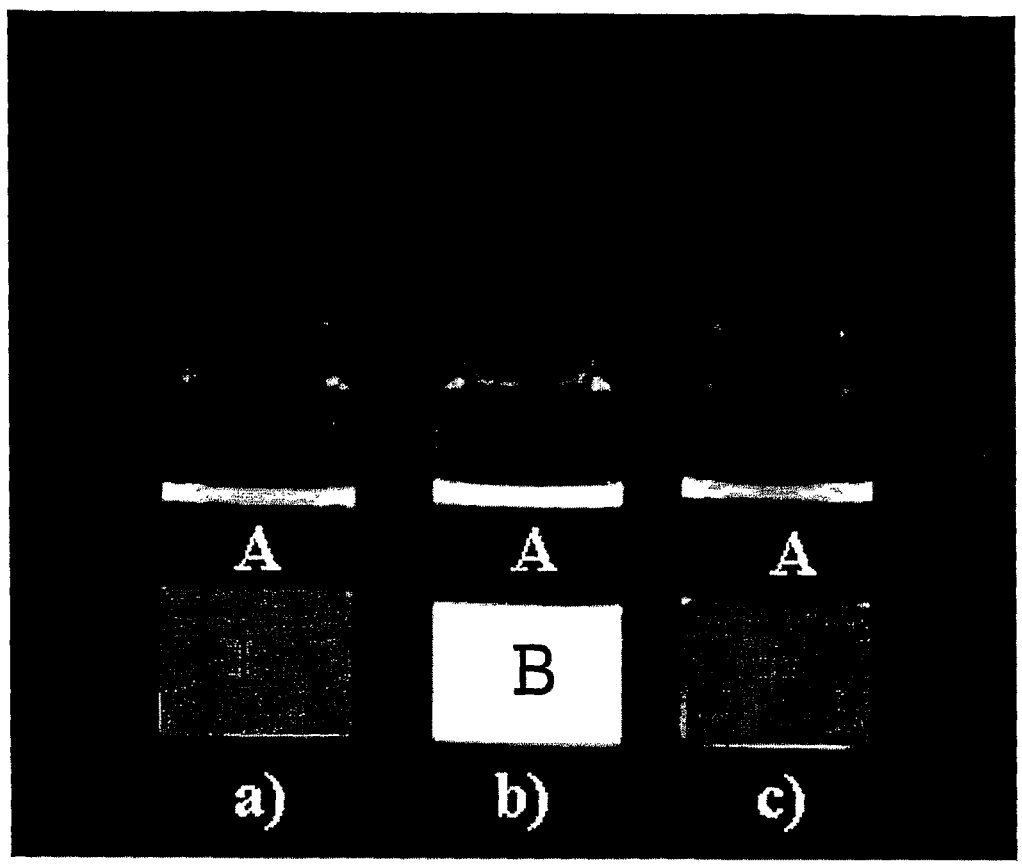
FIG. 3 is a fluorescent photograph of CdSe/ZnS dispersed with perfluoro materials [A: toluene, B: perfluoro rays, a) fluorescent ray of 430 nm, b) fluorescent ray of 525 nm, and c) fluorescent ray of 600 nm].

Preparation of Perfluorocarbon Nano-Emulsion Containing Quantum Dot Nano-Particles Surface Reforming of Quantum Dot Nano-Particles Using Perfluorocarbons 50 μL of quantum dot (QD) nano-particles with three colors (CdSe/Zn[430 nm, 525 nm, 600 nm], 1.4 mg/mL in toluene) (Evident Tech Co, USA) was added into methanol so that the total volume of the solution becomes 8 mL. When stratification was performed by adding 4 mL of perfluorocarbon into the solution, 0.5 mL of 1H,1H,2H,2H-perfluorodecanethiol (ALDRICH, USA) was slowly dropped into the solution. The stratified solution was strongly stirred until quantum dots move to a perfluorocarbon layer and a middle layer of perfluorocarbon and methanol layers (FIG. 3). After reaction was finished, the upper layer solution (the methanol layer) was poured, and the non-reacted 1H,1H,2H,2H-perfluorodecanethiol was removed by adding and mixing an excessive amount of methanol solution into the stratified solution. This procedure was repeated three times.

Preparation of Perfluorocarbon Nano-Emulsion Containing Qauntum Dot Nano-Particles The perfluorocarbon nano-emulsion of the present invention was completed by preparing a liposome for encapsulating the perfluorocarbon solution containing quantum dot nano-particles and then mixing the liposome with surface-reformed nano-particles and perfluorocarbons. The perfluorocarbons used were four kinds of perfluorocarbons. The four kinds of perfluorocarbons were individually used or combined. Here, the four kinds of perfluorocarbons were perfluorodecalin (PFD), perfluoro-15-crown-5ether (PECE), perfluorodioctylchloride (PFDOC) (SynQuest Laboratories, Inc, USA) and perfluorooctylbromide (PFOB) (Sigma-Aldrich, USA).

Specifically, 2.0 w/v surfactant mixture was first prepared using 64 mol % lecithin (Sigma chemical Co., USA), 35 mol % cholesterol (Sigma chemical Co., USA) and 1 mol % DPPE-PEG 2000 (Avanti Polar Lipids Inc., Alabaster, Ala., USA). After the surfactant mixture was dissolved in chloroform, a solvent was evaporated under a decompression device and dried in a vacuum oven at 50° C. for a day, thereby forming a thin lipid membrane. Sterilized tertiary distilled water is put into the lipid membrane and then dispersed by supersonic waves, thereby preparing a liposome suspension.

The perfluorocarbon nano-emulsion containing quantum dot nano-particles is prepared as follows. That is, sterilized distilled water is put into 40% (v/v) perfluorocarbon solution (PFC/QD) containing nano-particles, in which perfluorooctylbromide is used as the perfluorocarbon, 1.7% (w/v) glycerine (Sigma-Aldrich, USA) and the others. Then, the solution is mixed for 30 seconds using a homogenizer (Power Gen 1000, Fisher Scientific, USA). The mixed solution is emulsified at 2000 PSI for four minutes using M-110S microfluidics emulsifier (Microfluidics, USA). The prepared perfluorocarbon nano-emulsion containing quantum dot nano-particles is put into a vial. Then, the vial is sealed and kept at 4° C.

Examples 2 to 4

Preparation of Perfluorocarbon Nano-Emulsion Containing Quantum Dot Nano-Particles A perfluorocarbon nano-emulsions containing quantum dot nano-particles are prepared (Examples 2 to 4) in the same manner, except that the perfluorooctylbromide used in Example 1 is replaced with the combination of perfluorooctylbromide and perfluorodecalin (Example 2), the combination of perfluorooctylbromide, perfluorodecalin and perfluorodioctylchloride (Example 3), or the combination of perfluorooctylbromide, perfluorodioctylchloride and perfluoro-15-crown-5 ether (Example 4). The composition of the prepared nano-emulsion is shown in the following Table 1.

TABLE 1

Nano-emulsions containing quantum dot nano-particles according to the examples

| Classification | Nano-particle | Spreading solvent (perfluorocarbon) | Surfactant mixture |
|---|---|---|---|
| Example 1 | Cd/Se/ZnS | Perfluorooctylbromide (PFOB) | Lecithin, cholesterol DPPE-PEG2000 |
| Example 2 | Cd/Se/ZnS | Perfluorooctylbromide (PFOB) + perfluorodecalin (PFD) | Lecithin, cholesterol DPPE-PEG2000 |
| Example 3 | Cd/Se/ZnS | Perfluorooctylbromide (PFOB) + perfluorodecalin (PFD) + perfluorodioctylchloride (PFDOC) | Lecithin, cholesterol DPPE-PEG2000 |
| Example 4 | Cd/Se/ZnS | Perfluorooctylbromide (PFOB) + perfluorodioctylchloride (PFDOC) + perfluoro-15-crown-5ether (PFCE) | Lecithin, cholesterol DPPE-PEG2000 |

Experiment 1

Analysis of Multimodal Fluorescent and Multispectral MRI Characteristics for Perfluorocarbon Nano-Emulsion Containing Quantum Dot Nano-Particles MRI characteristics for the four kinds of perfluorocarbons are obtained using 600 MHZ Bruker NMR spectrometer (Avance DMX600, Ettlingen, Germany). The analysis results are shown in FIG. 2. In FIG. 2, (a) is an analysis result using PFOB, (b) is an analysis results using PFOB+PFD, (c) is an analysis result using PFOB+PFD+PFDOC, and (d) is an analysis result using PFOB+PFDOC+PFCE.

As a result obtained by analyzing MRI characteristics for the four kinds of perfluorocarbons, it can be seen that magnetic resonance spectral characteristics and images for the four kinds of perfluorocarbons are different from one another. That is, it can be seen that various multispectral MRI characteristics are obtained by varying the kind and combination of the used perfluorocarbons.

Figure 4:
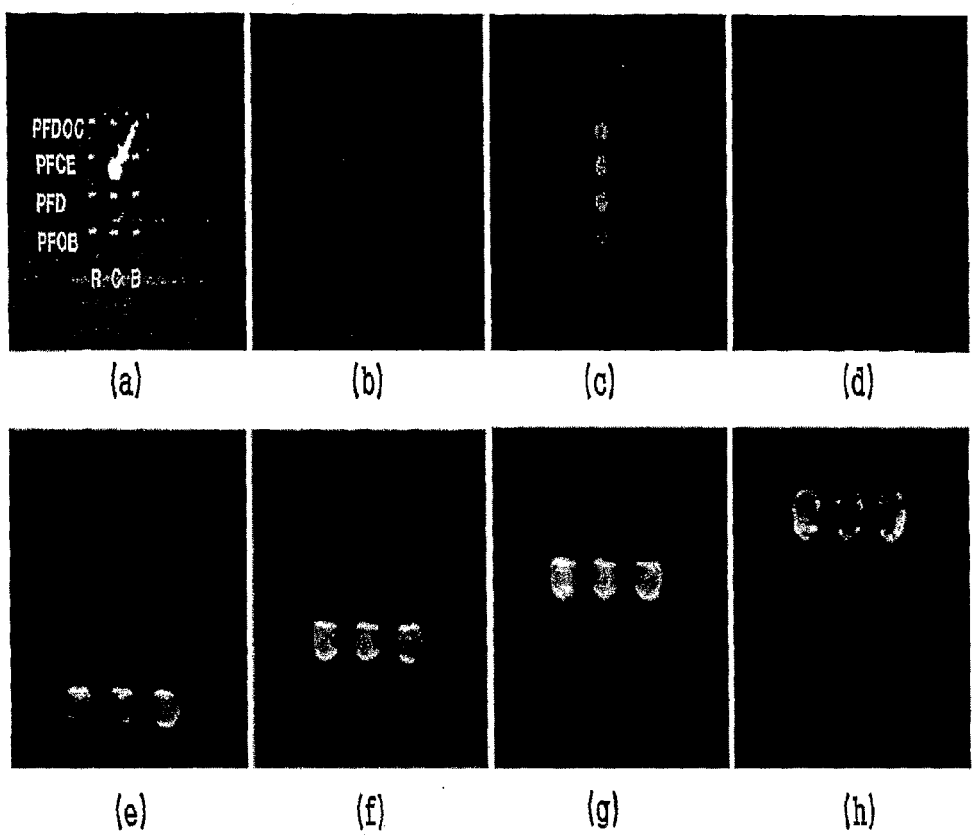
FIG. 4 illustrates multicolor fluorescent rays and multispectral MRI images using the prepared nano-material [(a) chromatic image, (b) red filter, (c) green filter, (d) blue filter, (e) PFOB-resonance selection, (f) PFD-resonance selection, (g) PFCE-resonance selection and (h) PFDOC-resonance selection].

$^{19}$F MRI images of the nano-emulsion containing quantum dot nano-particles are measured using 4.5 T MRI scanner (Bruker, Germany), and their results are shown in FIG. 4.

As shown in FIG. 4, it can be seen that the nano-emulsion of the present invention shows three multicolor fluorescent characteristics of red, blue and green as the result of fluorescent characteristics of the quantum dot nano-particles (CdSe/ZnS) used ((b), (c) and (d) of FIG. 4), and four selective MRI images are shown depending on the kind of the perfluorocarbons used. Therefore, it can be seen that 12 multimodal images are observed by combinations of four multispectral MRI images and three multicolor fluorescent rays.

Accordingly, quantum dot nano-particles emitting different rays are respectively capped with different materials, and perfluorocarbons having controlled resonance frequencies are respectively capped with other materials, thereby observing target materials corresponding to the number of combinations of the capped materials.

The invention claimed is:

1. A multimodal imaging method in vivo using a nano-emulsion comprising quantum dot nano-particles reformed with a perfluorocarbon for surface reforming, and $^{19}$F-containing perfluorocarbons, the method comprising:
   injecting the nano-emulsion in vivo to simultaneously perform multicolor ray emission of the quantum dot nano-particles and control of resonance frequencies in accordance with the kinds of $^{19}$F-containing perfluorocarbons (a first step);
   measuring the combined wavelength of the emitted rays and the controlled resonance frequency of the $^{19}$F-containing perfluorocarbons (a second step);

wherein the quantum dot nano-particles reformed with a perfluorocarbon for surface reforming are dispersed in the $^{19}$F-containing perfluorocarbons; and the perfluorocarbon for surface reforming is not a $^{19}$F-containing perfluorocarbon.

2. The method according to claim 1, wherein m×n multimodal images can be simultaneously obtained using combinations of multispectral MRI images and multicolor fluorescent rays, which obtained by combinations of the number (m) of kinds of the perfluorocarbons and the number (n) of the multicolor fluorescent rays generated from quantum dot nano-particles.

3. The method according to claim 1, wherein the quantum dot nano-particles has a structure in the form of a single core or core/shell and comprises compounds containing two or more elements from Group II-VI or III-V in the periodic table.

4. The method according to claim 1, wherein the $^{19}$F-containing perfluorocarbon containing the reformed quantum dot nano-particle is encapsulated in a lipid liposome.

5. The method according to claim 1, wherein the perfluorocarbon for surface reforming includes perfluorochemical having one end group selected from the group consisting of thiol, phosphine and phosphine oxide, or amphiphilic fluorinated hydrocarbon.

6. The method according to claim 1, wherein the perfluorocarbon for surface reforming includes one selected from the group consisting of perfluorinated alcohol phosphate ester and its salt, perfluorinated sulfonamide alcohol phosphate ester and its salt, perfluorinated alkyl sulfonamide alkylene quaternary ammonium salt, N,N-(carboxyl-substituted lower alkyl) perfluorinated alkyl sulfonamide, and a compound thereof.

7. The method according to claim 6, wherein the perfluorinated alcohol phosphate ester includes a free acid of mono or bis(1H,1H,2H,2H-perfluoroalkyl)phosphate derived diethanolamine salt.

8. The method according to claim 6, wherein the perfluorinated sulfonamide alcohol phosphate ester is one selected from the group consisting of perfluoro-n-octyl-N-ethysulfonamidoethyl phosphate, bis(perfluoro-n-octyl-N-ethylsulfonamidoethyl)phosphate, ammonium salt of bis(perfluoro-n-octyl-N-ethylsulfonamidoethyl)phosphate, bis (perfluorodecyl-N-ethylsulfonamidoethyl phosphate and bis (perfluorohexy-N-ethylsulfonamidoethyl)phosphate.

9. The method according to claim 2, wherein the multispectral magnetic resonance images are obtained by a $^{19}$F-containing perfluorocarbon or its derivative.

10. The method according to claim 9, wherein the $^{19}$F-containing perfluorocarbon includes at least one functional group connected to a main chain consisting of carbon atoms.

11. The method according to claim 9, wherein the $^{19}$F-containing perfluorocarbon is one selected from the group consisting of perfluorotributylamine (FC47), perfluorodecalin (PP5), perfluoromethyldecalin (PP9), perfluorooctylbromide, perfluorotetrahydrofuran (FC80), perfluoroether (PID) [(CF$_3$)$_2$CFOCF$_2$(CF$_2$)$_2$CF$_2$OCF(CF$_3$)$_2$], perfluoroether (PIID) [(CF)$_2$CFOCF$_2$(CF$_2$)$_6$CF$_2$OCF(CF$_3$)$_2$], perfluoroetherpolymer (Fomblin Y/01), perfluorododecane, perfluorobicyclo[4.3.0]nonane, perfluorotritrimethylbicyclohexane, perfluorotripropylamine, perfluoroisopropylcylcohexane, perfluomendotetrahydrodicyclopentodiene, perfluoroadamantane, perfluoroexotetrahydrodicyclopentadiene, perfluorobicyclo[5.3.0]decane, perfluorotetramethylcyclohexane, perfluoro-1-methyl-4-isopropylcyclohexane, perfluoro-n-butylcyclohexane, perfluorodimethylbicyclo[3.3.1]nonane, perfluoro-1-methyl-4-t-butylcyclohexene, perfluorodecahydroacenapthene, perfluoro-nundecane, perfluorotetradecahydrophenanthrene, perfluoro-1,3,5,7-tetramethyladamantane, perfluorododecahydrofluorene, perfluoro-1-3-dimethyladamantane, perfluoro-n-octylcyclohexane, perfluoro-7-methyl bicyclo[4.3.0]nonane, perfluoro-p-diisopropylcyclohexane, perfluoro-m-diisopropylcyclohexane, perfluoro-4-methyloctahydroquinolidizine, perfluoro-N-methyldecahydroquinoline, F-methyl-1-oxadecalin, perfluorooctahydroquinolidizine, perfluoro 5,6-dihydro-5-decene, perfluoro-4,5-dihydro-4-octene, perfluorodichlorooctane, perfluorobischlorobutyl ether, perfluorooctane, perfluorodichlorooctane, perfluoro-n-octylbromide, perfluoroheptane, perfluorodecane, perfluorocyclohexane, perfluoromorpholine, perfluorotripropylamine, perfluorotributylamine, perfluorodimethylcyclohexane, perfluorotrimethylcyclohexane, perfluorodicyclohexylether, perfluoro-n-butyltetrahydrofuran, perfluoro-15-crown-5ether and compounds structurally similar thereto.

* * * * *